United States Patent [19]
Twardowski et al.

[11] Patent Number: 4,772,269
[45] Date of Patent: Sep. 20, 1988

[54] PERITONEAL DIALYSIS CATHETER

[75] Inventors: Zbylut J. Twardowski; Karl D. Nolph, both of Columbia, Mo.

[73] Assignee: Curators of the University of Missouri, Columbia, Mo.

[21] Appl. No.: 14,161

[22] Filed: Feb. 11, 1987

Related U.S. Application Data

[63] Continuation of Ser. No. 729,185, May 1, 1985, abandoned.

[51] Int. Cl.$^4$ ............................................. A61M 25/00
[52] U.S. Cl. ..................................... 604/175; 604/29; 604/280
[58] Field of Search .................. 604/175, 29, 280, 281

[56] References Cited

U.S. PATENT DOCUMENTS

| | | | |
|---|---|---|---|
| 4,368,737 | 1/1983 | Ash | 604/175 |
| 4,437,856 | 3/1984 | Valli | 604/29 |
| 4,496,349 | 1/1985 | Consentino | 604/175 |
| 4,687,471 | 4/1987 | Twardowski et al. | |

FOREIGN PATENT DOCUMENTS 0081724  6/1983  European Pat. Off. ............ 604/175

OTHER PUBLICATIONS

The Need for a "Swan Neck" Permanently Bent, Arcuate Peritoneal Dialysis Catheter, *Peritoneal Dialysis Bulletin*, Oct.–Dec., 1985 pp. 219-223.
Prolonged Peritoneal Dialysis for Chronic Renal Failure, *The Lancet*, Mar. 28, 1964, pp. 700-702.
"A Bacteriologically Safe Peritoneal Access Device", Tenckhoff et al. (Trans. ASAIP 1968) pp. 181-187.
"Home Peritoneal Dialysis", Tenckhoff [*Clinical Aspects of Urema & Dialysis*, (1976)] pp. 583-615.
"Can New Catheter Design Eliminate Exit-Site and Tunnel Infections?", Twardowski et al. (Perspective in Peritoneal Dialysis vol. 4, No. 2, 12/86).

*Primary Examiner*—Stephen C. Pellegrino
*Attorney, Agent, or Firm*—Charles R. Mattenson; Paul C. Flattery; Daniel D. Ryan

[57] ABSTRACT

A peritoneal catheter comprises a flexible catheter tube carrying porous cuff means to facilitate permanent securance of the catheter to the abdominal wall. The catheter tube defines, in its natural, unstressed condition, a bent segment adjacent the porous cuff means. This permits the catheter to be mounted in a tunnel formed through the abdominal wall in relatively unstressed configuration with both ends pointing downwardly.

4 Claims, 1 Drawing Sheet

PERITONEAL DIALYSIS CATHETER

This is a continuation of application Ser. No. 729,185, filed May 1, 1985, now abandoned.

TECHNICAL FIELD

The Tenckhoff catheter is commercially available and widely used with patients who must undergo chronic peritoneal dialysis for maintenance in the absence of normal kidney function. The catheter is made of silicone rubber, and has a pair of porous tissue attachment cuffs in spaced relation to each other, so that after implantation of the catheter into the abdominal wall, tissue grows into pores of the cuffs, for secure and permanent anchoring of the catheter in place. In the article by Tenckhoff and Schechter entitled A Bacteriologically Safe Peritoneal Access Device, Trans. Am. Soc. Artif. Intern. Organs 1968; 14: 181–187, the authors disclosed their new catheter and showed an arcuate subcutaneous catheter tunnel, so that both the external and internal end segments of the catheter were generally directed in a caudal direction (i.e., downwardly, toward the feet of the patient).

In the practice of installation of such peritoneal catheters, this technique is often followed, so that both the outer end of the catheter outside of the body and lying over the skin, and the inner end of the catheter within the peritoneal cavity, typically point downwardly toward the pelvis or feet.

However, known peritoneal catheters have been molded and cured in generally straight configuration, so that their natural, unstressed configuration is a straight line, although the catheters are flexible and may be placed in other configurations. Accordingly, peritoneal catheters of the prior art must be stressed by bending into a substantially U-shape, in order to be installed into a curved tunnel through the abdominal wall, which holds the catheter in its downward facing, U-shaped position so that both ends of the catheter extend downwardly.

Significant advantages have been found for this arrangement. For example, in currently unpublished data by authors including us, it has been statistically shown that patients who have downwardly caudally pointing outer ends of their peritoneal catheter have fewer days of catheter tunnel infection, when compared with patients whose catheter ends point either upwardly or in a sideward direction.

Currently however, disadvantages of this arrangement also exist. First, it appears that the elastic memory of the catheter, which urges it to assume its original, unstressed, straight configuration, can cause catheter cuffs to be expelled from the tunnel site in a slow, migratory process. This of course is most disadvantageous. Secondly, the inner end portion of the catheter can migrate upwardly with greater ease, due to the internal stresses of the catheter tending to urge it straight. It is undesirable for the catheter to migrate upwardly to upper portions of the peritoneal cavity, where it is prone to omental wrapping and one way obstruction of flow through the catheter. Accordingly, there is a need to keep the inner catheter portion positioned in the lower portions of the peritoneal cavity, adjacent the pelvis.

In accordance with this invention, the above disadvantages are reduced by the use of a modified catheter.

DESCRIPTION OF THE INVENTION

In this invention, a peritoneal catheter comprises a flexible catheter tube, which may be made of silicone rubber or equivalent material. The tube has a proximal and a distal end portion. The distal end portion defines flow port means for fluid communication between the bore of the catheter tube and the peritoneal cavity. The catheter also carries porous cuff means to facilitate permanent securance of the catheter to the abdominal wall.

In accordance with this invention, the catheter tube defines, in its natural, unstressed condition, a bent segment adjacent the porous cuff means. As the result of this, the catheter can be mounted in a tunnel formed through the abdominal wall in relatively unstressed condition, with the bent segment being mounted in the tunnel. Hence, the proximal end portion of the catheter may extend outwardly from the abdominal wall and downwardly from the outer end of the tunnel, while the distal end portion of the catheter extends inwardly and downwardly from the inner end of the tunnel.

Because of the unstressed bent segment, the catheter of this invention may occupy the desirable position where both ends thereof point caudally or downwardly, while at the same time the catheter tube is in relatively natural, unstressed condition when compared with prior art catheters which have been placed in such a position. Thus, less urging force is present in the catheter to cause gradual expulsion of cuffs from the tunnel formed in the abdominal wall. Also, less force is present urging the distal end portion of the catheter upwardly out of its desired position in a lower portion of the peritoneal cavity.

Additionally, the installed catheter of this invention can exhibit significantly reduced days of tunnel infection which the patient must endure, because of the downward pointing aspect of the proximal end portion of the catheter. It is believed that downwardly pointing proximal end portions of peritoneal catheters permit improved draining from the tunnel area in the event of an infection, which can significantly reduce the severity of the infection. Also, less contamination of the tunnel site takes place because of the migration of sweat and bacteria-laden water into the tunnel area, because its outer end points downwardly along with the proximal end portion of the catheter.

It is generally preferred for the bent segment of the catheter to define an arc of 90° to 180° so that the proximal and distal end portions form an angle to each other that is supplementary to the angle of said arc. A "supplementary" angle is an angle which, when combined with the arc angle, totals 180°. Accordingly, if the arc of the bent segment is 120°, the proximal and distal end portions will form an angle with each other of 60°. Most preferably, the bent segment defines an arc of about 120° to 170°.

The use of a bent segment which defines an arc makes possible the formation of a substantial angle in the catheter, as shown in the drawings, without the danger of kinking of the catheter, as might take place if a merely angled corner were used rather than an arc.

The porous cuff means on the catheter may be any conventional cuff used for tissue attachment to a catheter. While a single, porous cuff may be used, it is preferable to use a pair of spaced, porous cuffs in the manner of the well-known Tenckhoff catheter as it is currently commercially available. The bent segment may be positioned between the spaced, porous cuffs.

DESCRIPTION OF SPECIFIC EMBODIMENTS

Figure 1:
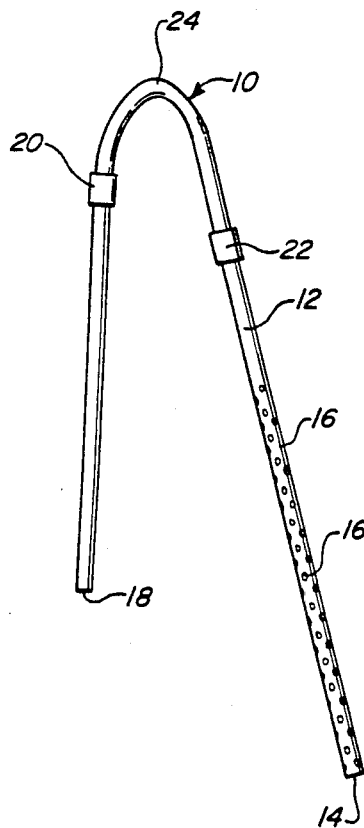
FIG. 1 is a plan view of one embodiment of the catheter of this invention in its natural, unstressed configuration.

Referring to the drawings, catheter 10 is a peritoneal catheter generally of the design of a commercially available Tenckhoff catheter, except as otherwise described herein. Catheter 10 comprises a flexible catheter tube 12 which may be made of silicone rubber or any other desired and appropriate material. Adjacent the distal end 14 of the catheter, a plurality of flow ports 16 are formed in the wall of the catheter, while distal end 14 itself may be open as well, for added flow communication between the exterior and the bore of catheter 10.

Proximal end 18 defines an open bore as well for receiving typically a titanium adaptor of known design, to provide connection with a transfer set or other means for flow communication with peritoneal dialysis solution containers.

A pair of cuffs 20, 22 of known design are also provided. Outer cuff 20 is intended to be positioned within the abdominal wall tunnel about 2 centimeters from the outer skin, while cuff 22 is positioned adjacent the inner end of the abdominal tunnel. The abdominal tunnel may be formed by the surgeon when the catheter is installed in the patient's abdomen.

In accordance with this invention, catheter 10 defines, in its natural, unstressed condition, a bent segment 24. As shown, bent segment 24 defines an arc which may most preferably extend on the order of 150°–170°. A catheter may be manufactured with such an unstressed bend by molding the catheter, or causing it to be cross-linked, while in the desired bent, position.

Figure 2:
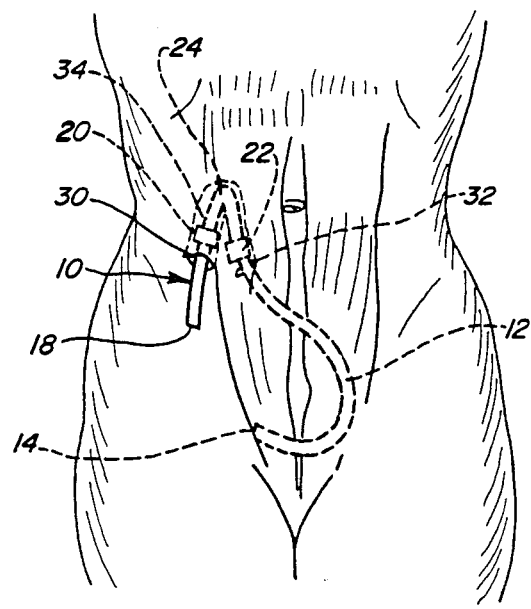
FIG. 2 is a generally schematic view of the catheter of FIG. 1 as it may preferably be installed in the peritoneal cavity of a patient.

FIG. 2 illustrates how the catheter may be installed in the peritoneal cavity of the patient, with proximal end 18 projecting outwardly from the outer end 30 of the tunnel 34 formed by the surgeon in the abdominal wall. Distal end 14 of the catheter projects downwardly from the inner end 32 of the tunnel formed by the surgeon. Accordingly, since bent segment 24 is not as stressed as the catheters of prior art, there is less urging force to cause the distal end portion of the catheter to migrate upwardly in the peritoneal cavity.

It is generally preferable for tunnel 34 to be formed on one side of the patient, spaced from the midline of said patient. Also, proximal end 18 may be positioned at a small angle to the midline of the patient, with tunnel 34 being angled slightly to the left and downwardly in its outer portion, as shown in FIG. 2. A statistical analysis of the frequency and severity of infections made by a group included us have found that downwardly directed tunnels 34, which may extend slightly to the left, provide the lowest number of days of tunnel infection that a patient must endure, when compared with any other position of tunnel 34. We found that four catheters, installed in patients for a total of 2,136 days, in which the outer portions of the tunnels 34 extended in a direction no more than 45° away from straight down in the standing patient, resulted in no tunnel exit site infection at all. For catheter installations having higher angles than this from the straight down direction, increasing difficulties with tunnel site infection were encountered, which grew progressively worse as the angle grew larger, and was worst of all when the tunnel site exit pointed generally upwardly. FIG. 2 shows an ideal placement of the catheter of this invention in the abdomen.

The above has been offered for illustrative purposes only, and is not intended to limit the scope of the invention of this application, which is as defined in the claims below.

That which is claimed is:

1. A peritoneal catheter which comprises a flexible catheter tube having a proximal and a distal end portion, said distal end portion defining flow port means for fluid communication between the bore of the catheter tube and the peritoneal cavity, said catheter carrying spaced porous cuff means to facilitate permanent securance of the catheter to the abdominal wall, the improvement comprising, in combination:

said catheter tube defining, in its natural, unstressed condition, a bent segment forming an arc in a range of 100° to 180° between said porous cuff means, said bent segment, in use, extending in a tunnel formed through the abdominal wall in its relatively unstressed configuration to direct the distal end portion toward a caudel direction within the peritoneal cavity of the patient while the proximal end also projects, when viewed by an onlooker, downwardly.

2. The peritoneal catheter of claim 1 in which said proximal and distal end portions form an angle to each other that is supplementary thereto.

3. The peritoneal catheter of claim 2 in which said arch is defined in a range of 120° to 170°.

4. The peritoneal catheter of claim 1 in which said flexible catheter tube is made of silicone rubber.

* * * * *

REEXAMINATION CERTIFICATE (1705th)
United States Patent [19]
Twardowski et al.

[11] B1 4,772,269
[45] Certificate Issued May 19, 1992

[54] PERITONEAL DIALYSIS CATHETER

[75] Inventors: Zbylut J. Twardowski; Karl D. Nolph, both of Columbia, Mo.

[73] Assignee: Curators of the University of Missouri, The

Reexamination Request:
No. 90/002,408, Aug. 19, 1991

Reexamination Certificate for:
Patent No.: 4,772,269
Issued: Sep. 20, 1988
Appl. No.: 14,161
Filed: Feb. 11, 1987

Related U.S. Application Data

[63] Continuation of Ser. No. 729,185, May 1, 1985, abandoned.

[51] Int. Cl.⁵ .............................................. A61M 25/00
[52] U.S. Cl. ...................................... 604/175; 604/29; 604/280
[58] Field of Search ................ 604/29, 175, 280, 281

[56] References Cited

U.S. PATENT DOCUMENTS 4,368,737  1/1983  Ash ..................................... 604/175
4,437,856  3/1984  Valli .................................... 604/29
4,496,349  1/1985  Cosentino .......................... 604/175

FOREIGN PATENT DOCUMENTS 146777  6/1984  Denmark .
81724   6/1983  European Pat. Off. ............ 604/175

OTHER PUBLICATIONS

Handbook of Silicone Rubber Fabrication, Wilfred Lynch 1978 p. 36.

*Primary Examiner*—Stephen C. Pellegrino

[57] ABSTRACT

A peritoneal catheter comprises a flexible catheter tube carrying porous cuff means to facilitate permanent securance of the catheter to the abdominal wall. The catheter tube defines, in its natural, unstressed condition, a bent segment adjacent the porous cuff means. This permits the catheter to be mounted in a tunnel formed through the abdominal wall in relatively unstressed configuration with both ends pointing downwardly.

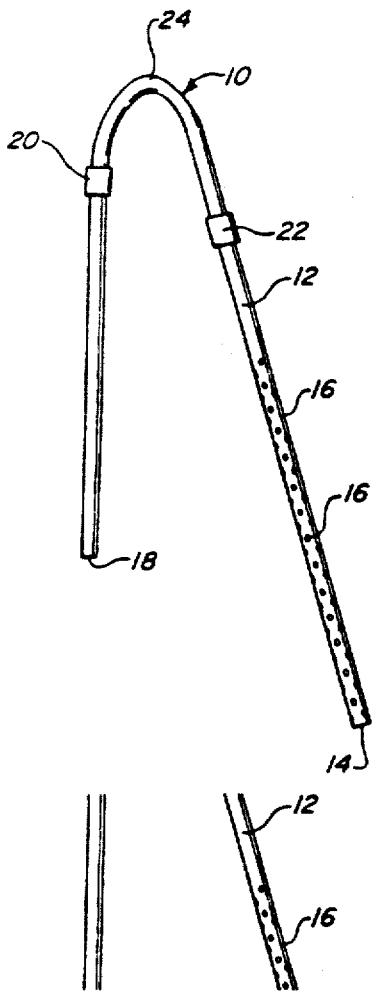

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

* * * * *